United States Patent
Raskin et al.

(12)

(10) Patent No.: US 7,294,132 B2
(45) Date of Patent: *Nov. 13, 2007

(54) RADIALLY PORTED NEEDLE FOR DELIVERING BONE GRAFT MATERIAL AND METHOD OF USE

(75) Inventors: Keith B. Raskin, New York City, NY (US); Brian R. Harris, Jr., Cordova, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 393 days.

This patent is subject to a terminal disclaimer.

(21) Appl. No.: 10/678,701

(22) Filed: Oct. 3, 2003

(65) Prior Publication Data

US 2004/0133211 A1 Jul. 8, 2004

Related U.S. Application Data

(60) Provisional application No. 60/415,503, filed on Oct. 3, 2002.

(51) Int. Cl.
*A61B 17/58* (2006.01)
*A61F 2/00* (2006.01)

(52) U.S. Cl. .................................................. 606/92

(58) Field of Classification Search .............. 606/53, 606/86, 92, 93, 94; 604/134, 135, 152, 154, 604/155, 97.01, 97.02, 97.03, 187–189, 218, 604/224, 227; 433/89, 90
See application file for complete search history.

(56) References Cited

U.S. PATENT DOCUMENTS

| | | | | | |
|---|---|---|---|---|---|
| 4,653,487 | A | * | 3/1987 | Maale | 606/62 |
| 5,380,276 | A | * | 1/1995 | Miller et al. | 604/28 |
| 5,800,407 | A | * | 9/1998 | Eldor | 604/264 |
| 6,019,765 | A | * | 2/2000 | Thornhill et al. | 606/94 |
| 6,048,346 | A | * | 4/2000 | Reiley et al. | 606/92 |
| 6,127,597 | A | * | 10/2000 | Beyar et al. | 606/86 |
| 6,241,710 | B1 | * | 6/2001 | VanTassel et al. | 604/272 |
| 6,506,214 | B1 | * | 1/2003 | Gross | 623/19.11 |
| 6,645,213 | B2 | * | 11/2003 | Sand et al. | 606/92 |
| 6,899,716 | B2 | * | 5/2005 | Cragg | 606/86 |
| 2002/0010472 | A1 | * | 1/2002 | Kuslich et al. | 606/93 |
| 2002/0123723 | A1 | * | 9/2002 | Sorenson et al. | 604/164.01 |
| 2003/0036762 | A1 | * | 2/2003 | Kerr et al. | 606/93 |

* cited by examiner

*Primary Examiner*—Anuradha Ramana

(57) ABSTRACT

A radially ported bone graft needle, particularly useful in minimally invasive procedures, is provided. The bone graft needle delivers bone graft material to a bone defect area by extruding the bone graft material both axially and radially simultaneously.

16 Claims, 4 Drawing Sheets

RADIALLY PORTED NEEDLE FOR DELIVERING BONE GRAFT MATERIAL AND METHOD OF USE

RELATED APPLICATIONS

This application claims priority to U.S. Provisional Patent Application Serial No. 60/415,503, filed Oct. 3, 2002.

This application is related to Assignee's Co.-pending U.S. patent application Ser. No. 10/679.077, filed the same day as this patent application.

BACKGROUND OF THE INVENTION

1. Field of the Invention

The present invention generally pertains to the use of graft materials for promoting bone growth and, more particularly, to ported needles for delivering bone graft materials to metaphysical compression fractures, other bone voids or other bone defect areas.

2. Discussion of the Prior Art

In the past, bone graft materials have been delivered to bone defect areas, such as metaphysical compression fractures or bone voids as well as other areas of bone structures having discontinuities, cavities, recesses or the like (hereinafter referred to as bone defect areas). Minimally invasive bone graft procedures are preferred in many cases, and the delivery or injection of bone graft material to the bone defect areas has been accomplished using a needle having an open distal end forming an axial port for delivering the bone graft material to the bone defect areas from a syringe coupled with the proximal end of the needle. Since the only opening for delivery of the bone graft material is the axial port, the prior art needle has the disadvantages of: (1) being unable to deliver bone graft material when the axial port abuts bone or other tissue, (2) not being able to radially inject bone graft material, and (3) requiring undesirable excessive force to eject bone graft material through the axial port.

SUMMARY OF THE INVENTION

Accordingly, it is an object of the present invention to overcome the above mentioned disadvantages of the prior art by providing a radially ported bone graft needle particularly useful in minimally invasive procedures. Another object of the present invention is to deliver bone graft material to a bone defect area by extruding the bone graft material both axially and radially simultaneously.

A further object of the present invention is to fill a bone defect area by radial, multiaxial and/or multidirectional delivery of bone graft material. The present invention is generally characterized in a bone graft needle having at least one radial opening or port for delivering bone graft material radially to a bone defect area.

The needle preferably has an axial opening or port allowing simultaneous axial and radial delivery of bone graft material. Preferably, equally spaced radial ports are arranged around the axial port; however, the size, arrangement and configuration of the radial ports can be varied dependent upon particular situations.

The present invention is further generally characterized in a method of delivering bone graft material to a bone defect area including the steps of placing the distal end of an elongate tubular delivery member of a bone graft needle adjacent the bone defect area and flowing the bone graft material through the delivery member to exit both radially and axially of the delivery member.

Some of the advantages of the present invention over the prior art are that both axial and radial delivery of bone graft material at a bone defect area can be achieved, radial delivery of bone graft material at a bone defect area can be achieved producing a more even distribution of bone graft material, bone graft material can be delivered even when the axial distal end opening of the needle is blocked, and reduced pressure is required to deliver bone graft material to a bone defect area.

BRIEF DESCRIPTION OF THE DRAWINGS

Other objects and advantages of the present invention will become apparent from the following description of the preferred embodiments taken in conjunction with the accompanying drawings, wherein like parts in each of the several figures are identified by the same reference characters.

DESCRIPTION OF THE PREFERRED EMBODIMENTS

Figure 1:
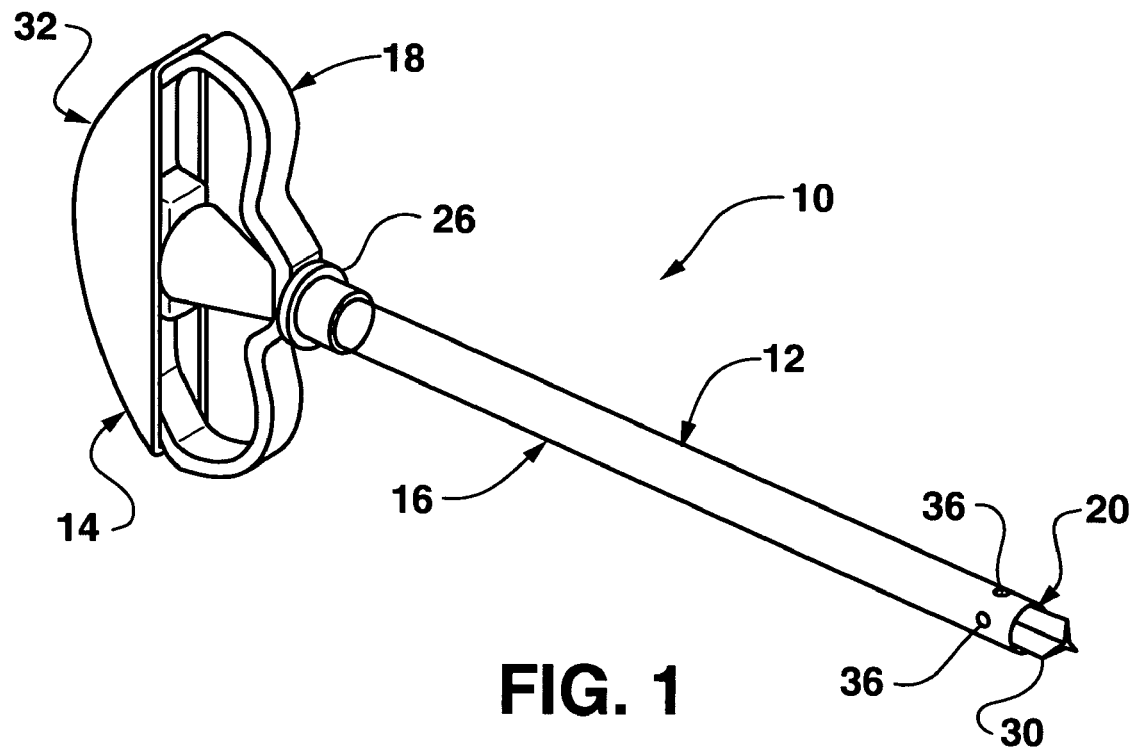
FIG. 1 is a perspective view of an instrument assembly incorporating a bone graft needle according to the present invention.
Figure 2:
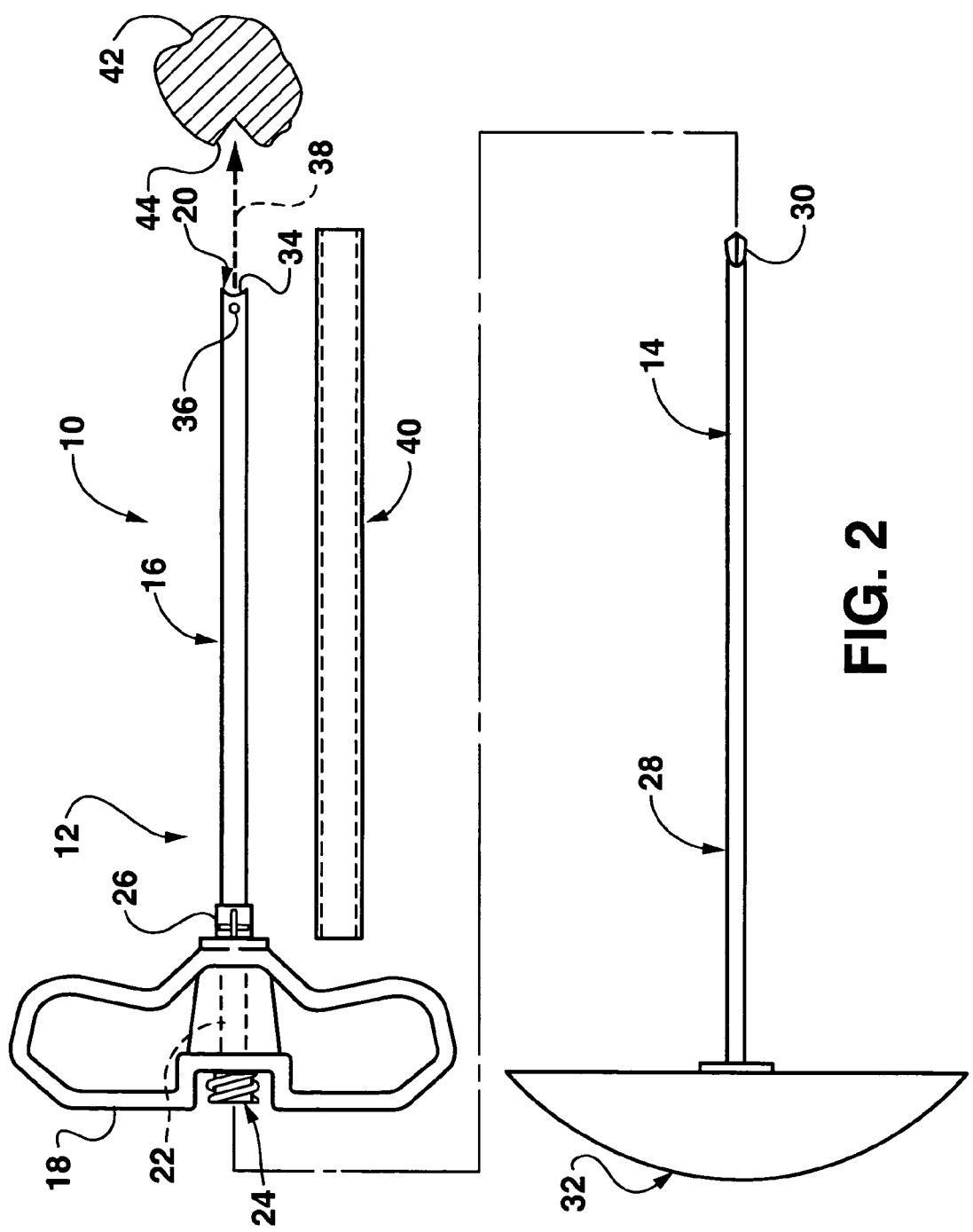
FIG. 2 is an exploded side view of the instrument assembly including a side view of the bone graft needle of the present invention.

The present invention relates to a bone graft needle used to deliver bone graft material to a bone defect area in a patient's body in a minimally invasive procedure in which the bone defect area is accessed via a minimal portal or incision. FIGS. 1 and 2 illustrate an instrument assembly 10 comprising a bone graft needle 12 and a penetrating member 14, such as a trocar. The bone graft needle 12 comprises an elongate tubular delivery member 16 extending distally from a handle 18. The delivery member 16 has an open distal end 20 communicating with a longitudinal passage 22 extending entirely through the delivery member 16 and the handle 18. A hollow coupling 24 having open distal and proximal ends is disposed at a proximal end of passage 22 with the interior of the coupling 24 in communication with the passage 22. The coupling 24 is designed for releasable attachment to a standard syringe and may be designed as a conventional luer lock coupling. The handle 18 can have various configurations to facilitate grasping. A proximal end of the delivery member 16 can be attached to the handle 18 via a hub 26 or in any desired manner. The proximal end of the delivery member 16 can extend any desired distance into a passage of the handle 18 or can extend entirely through the handle. The coupling 24 can be attached to the handle 18 in various ways or may be formed integrally, unitarily with the handle. The distal end of the coupling 24 can extend any desired amount into the passage of the handle 18. Accordingly, it should be appreciated that the longitudinal passage 22 can be formed in its entirety by the lumen of delivery member 16, can be formed in part by the lumen of the delivery member 16 and by a passage in handle 18, or can be formed in part by the lumen of delivery member 16, a passage in the handle 18 and the interior of the coupling 24.

Figure 3:
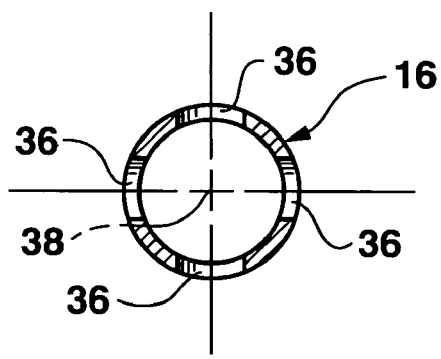
FIG. 3 is a sectional view of a delivery member of the bone graft needle taken along line A-A of FIG. 2.

The delivery member 16, as best shown in FIGS. 2 and 3, has an external cross sectional diameter or size for insertion through a minimally invasive portal or incision formed in the patient's body to access a bone defect area. The delivery member 16 has an internal cross-sectional diameter or size to receive the penetrating member 14 therethrough. As shown in FIGS. 1 and 2, the penetrating member 14 includes an elongate shaft 28 having a tissue penetrating distal end 30 and having a proximal end attached to a hub 32. The shaft 28 is insertable in the passage 22 extending entirely through the bone graft needle and, when the hub 32 is in abutment with the handle 18, the tissue penetrating distal end 30 protrudes distally from the open distal end 20 of the delivery member 16 as shown in FIG. 1. The instrument assembly 10 formed when the penetrating member 14 is inserted in the delivery member 16 can be utilized to form a minimally invasive portal in anatomical tissue of a patient to establish access to a bone defect area. The exposed tissue penetrating distal end 30 of the penetrating member is used to penetrate the anatomical tissue to introduce the distal end 20 of delivery member 16 at or near the bone defect area. Thereafter, the penetrating member 14 can be removed from the bone graft needle 12 leaving the bone graft needle in place to maintain the thusly formed portal with the handle 18 disposed externally of the patient's body. It should be appreciated, however, that the bone graft needle 12 can be used independently of a penetrating member and that the bone graft needle can be introduced at or near a bone defect area via a pre-established portal.

The open distal end 20 of delivery member 16 is circumscribed by a circumferential edge 34 that is provided with one or more proximally curving indentations as best shown in FIG. 2. Accordingly, the circumferential edge 34 comprises one or more distal most edge segments or points and one or more proximal most edge segments or points spaced proximally from the one or more distal most edge segments or points. A plurality of radial ports or openings 36 are formed through delivery member 16 proximally of circumferential edge 34. As shown in FIG. 3, four radial ports 36 are formed through the wall of delivery member 16 at spaced locations about a central longitudinal axis 38 of delivery member 16. The ports 36 are shown as being equally spaced about the central longitudinal axis 38 at 90 degree spaced locations about the central longitudinal axis 38. It should be appreciated, however, that the ports 36 can be equally spaced or variably spaced about the central longitudinal axis. The ports 36 are shown as having a circular perimetrical configuration, but the ports can have other perimetrical configurations including oval, elliptical and various longitudinally elongated perimetrical configurations. Each port 36 has a longitudinal dimension in a direction parallel to the central longitudinal axis 38. In the case of ports 36, the longitudinal dimension corresponds to the diameter of the ports. Each port 36 begins a distance D proximally of the proximal most edge segment or point of circumferential edge 34 as shown in FIG. 2. Where the circumferential edge is disposed in its entirety in a plane perpendicular to the central longitudinal axis 38, the proximal most edge segment or point will be disposed in the plane perpendicular to the central longitudinal axis 38 as described below for FIGS. 6 and 7. Distance D may be in the range of 0.020 inch to 0.275 inch. For delivery member 16 having ports 36 that are 0.063 inch in diameter, the longitudinal dimension for ports 36 is also 0.063 inch and a preferred range for distance D is 0.0505 inch to 0.0805 inch. FIG. 2 illustrates a removable tubular sheath 40 that may be disposed over the delivery member 16 prior to use.

In a preferred embodiment for bone graft needle 12, the needle is a 4 inch needle with delivery member 16 made of 304 stainless steel or other rigid biocompatible material and having a J-type cannulated distal end or tip; the delivery member is 0.185 inch in diameter; the radial ports 36 are 0.063 inch in diameter with centers at 90° (+ or −2.0°) spaced locations about the central longitudinal axis; and the centers of ports 36 are located 0.082 inch (+0.030 inch, −0.000 inch) proximally of the proximal most edge segment or point of circumferential edge 34. The needle 12 may be a JAMSHIDI—type needle with a luer-lock coupling or connector.

The open distal end 20 defines an axial or longitudinal port for delivery member 16 from which a bone graft material is discharged from delivery member 16 in an axial or longitudinal direction. The radial ports 36 permit bone graft material to be discharged from delivery member 16 in a direction radial to the central longitudinal axis 38 so that bone graft material is discharged radially simultaneously with the axial discharge.

In a method according to the present invention, the distal end 20 of delivery member 16 is introduced at or near a bone defect area in a patient's body via a minimally invasive portal providing access to the bone defect area from externally of the patient's body. As discussed above, the bone graft needle 12 may be assembled with a penetrating member to form an instrument assembly that may be used to form the portal. Visualization of the bone defect area may be accomplished using a remote viewing device, such as a fluoroscope or x-ray device, as conventionally utilized in minimally invasive procedures. FIG. 2 illustrates a bone segment 42 having a bone defect area 44 to be supplied with a bone graft material delivered via the bone graft needle 12. The bone defect area 44 may include metaphysical compression fractures, bone voids, discontinuities, cavities, recesses, non-unions or the like. The bone graft material to be delivered to the bone defect area may be any synthetic or tissue-based material that promotes bone growth and may be provided in paste form. Representative bone graft materials include calcium sulfate, as represented by the OSTEOSET® bone graft substitute of Wright Medical Technology, Inc., Allomatrix® and MIIG™ 115 of Wright Medical Technology, Inc., and demineralized bone matrix. The bone graft material is supplied to the bone graft needle 12 via a conventional syringe coupled with the coupling 24. With the handle 18 disposed externally of the patient's body, the syringe containing the bone graft material is coupled with coupling 24. The distal end 20 of delivery member 16 is positioned at or adjacent the bone defect area 44 and, depending on the size of the bone defect area, the distal end 20 may be positioned within the bone defect area. With the distal end 20 properly positioned, a plunger of the syringe is depressed to fill the passage 22 with the bone graft material. Depressing the plunger of the syringe pressurizes the bone graft material in passage 22 causing the bone graft material to be simultaneously discharged axially through distal end 20 and radially through the ports 36 to fill the bone defect area 44. In the case of delivery member 16, the bone graft material is discharged simultaneously in five directions, i.e. in a first direction axially or longitudinally through distal end 20 and in second, third, fourth and fifth radial directions through ports 36, respectively. In the event that the distal end 20 is in abutment with bone or other anatomical tissue, plugging or clogging of the delivery member 16 is avoided since discharge of the bone graft material continues through ports 36. In addition, back pressure is reduced for easier injection of the bone graft material since resistance to injection is reduced due to the multi-directional discharge provided by opening 20 and ports 36. The arrangement of ports 36 along the circumference of delivery member 16 permits radial discharge and distribution of the bone graft material and allows the bone defect area to be filled radially as well as from the distal end 20 of the delivery member. The distribution of ports 36 along the circumference of the delivery member allows the bone defect area to be filled in a range of 360 degrees around the delivery member. Also, the circumferential distribution of the ports 36 provides a more even and more balanced distribution of bone graft material to the bone defect area. Once the bone defect area 44 has been sufficiently supplied or filled with the bone graft material, the needle 12 is removed from the patient's body through the portal. The bone graft material remains in the patient's body to promote bone growth or regeneration.

Figure 4:
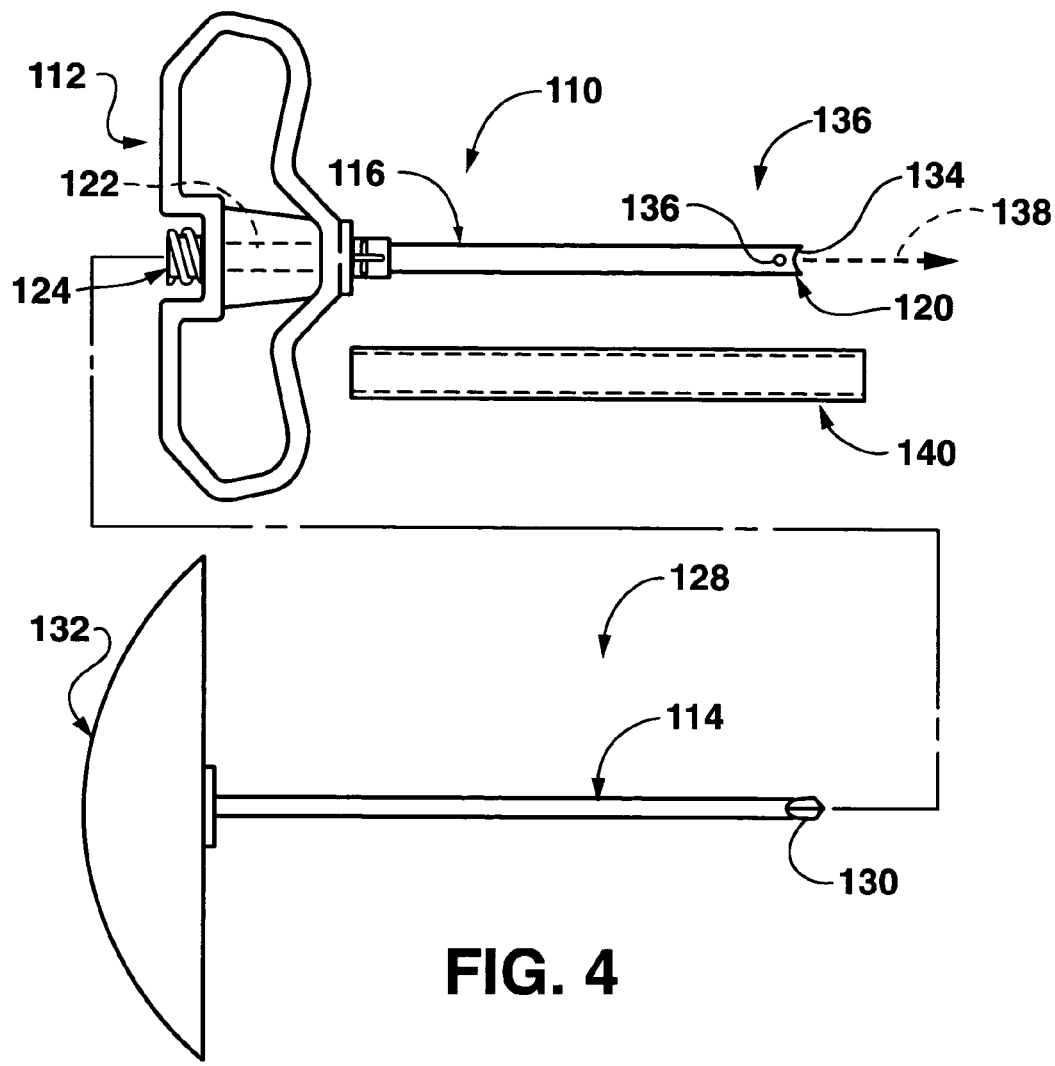
FIG. 4 is an exploded side view of an alternative instrument assembly incorporating an alternative bone graft needle according to the present invention.
Figure 5:
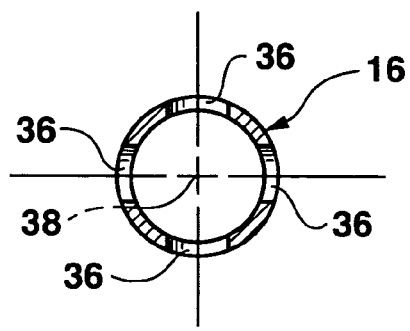
FIG. 5 is a sectional view of the delivery member of the alternative bone graft needle taken along lines B-B of FIG. 4.

FIG. 4 illustrates an alternative instrument assembly 110 comprising a bone graft needle 112 and a penetrating member 114. The instrument assembly 110 is similar to instrument assembly 10 except that the bone graft needle 112 and the penetrating member 114 are shorter in length than the bone graft needle 12 and penetrating member 14. Accordingly, it should be appreciated that the bone graft needle, as well as the penetrating member, can be provided in different lengths depending on the length needed to access the bone defect area. The bone graft needle 112 also differs from the bone graft needle 12 in that the delivery member 116 is of smaller external diameter than the delivery member 16. It should be appreciated, therefore, that the delivery members of the bone graft needles can be provided in various diametric sizes. Of course, the shafts of the penetrating members can also be provided in various diametric sizes depending on the anatomical tissue to be penetrated. The radial ports 136 for delivery member 116 differ from the ports 36 in that the ports 136 are smaller in diameter.

In a preferred embodiment for bone graft needle 112, the external diameter of delivery member 116 is 0.115 inch; the ports 136 have a diameter of 0.047 inch with centers at 90° (+ or −2.0°) spaced locations about the central longitudinal axis 138; distance D may be in the range of 0.020 inch to 0.275 inch and is preferably in the range of 0.082 inch to 0.112 inch; the needle 112 is a 6 cm needle with delivery member 116 made of 304 stainless steel or other rigid biocompatible material and having a J-type cannulated distal end or tip; and the centers of ports 136 are located 0.082 (+0.030 inch, −0.000 inch) proximally of the proximal most edge segment or point of circumferential edge 134. The needle 112 may be a JAMSHIDI-type needle with a luer-lock coupling or connector.

Figure 6:
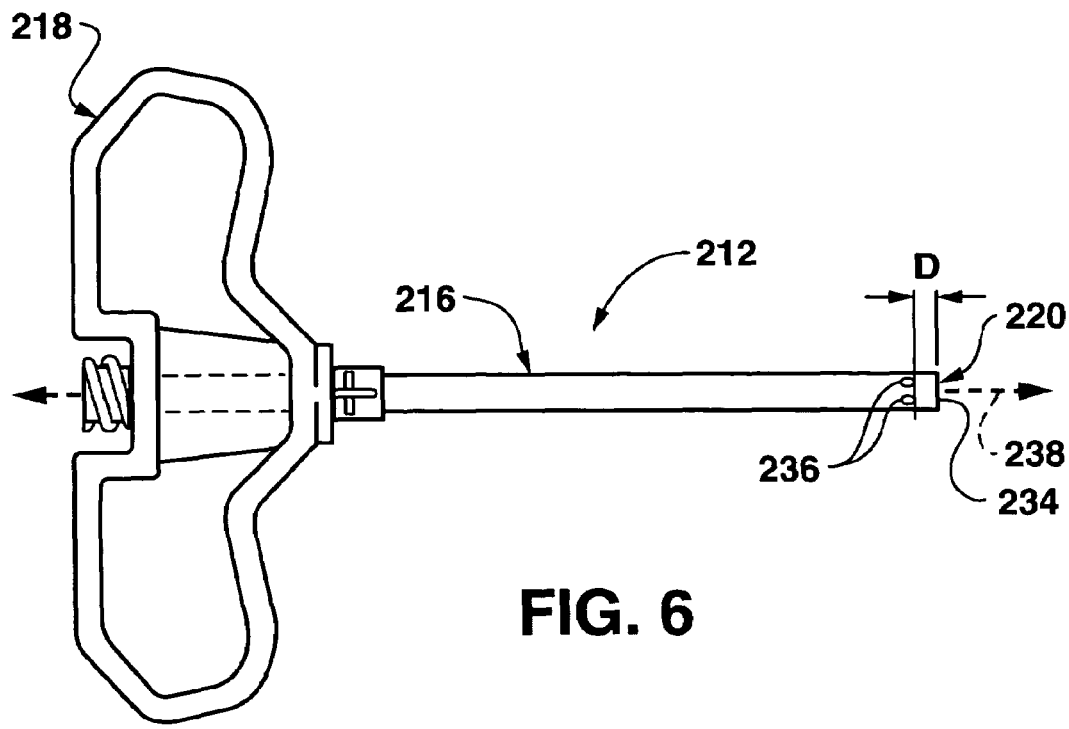
FIG. 6 is a side view of another alternative bone graft needle according to the present invention.

FIG. 6 is illustrative of a bone graft needle 212 in which the delivery member 216 has a distal end 220 with a circumferential edge 234 disposed in a plane perpendicular to the central longitudinal axis 238. Distance D for delivery member 216 is defined from the plane of edge 234 to where the ports 236 begin proximally of edge 234.

Figure 7:
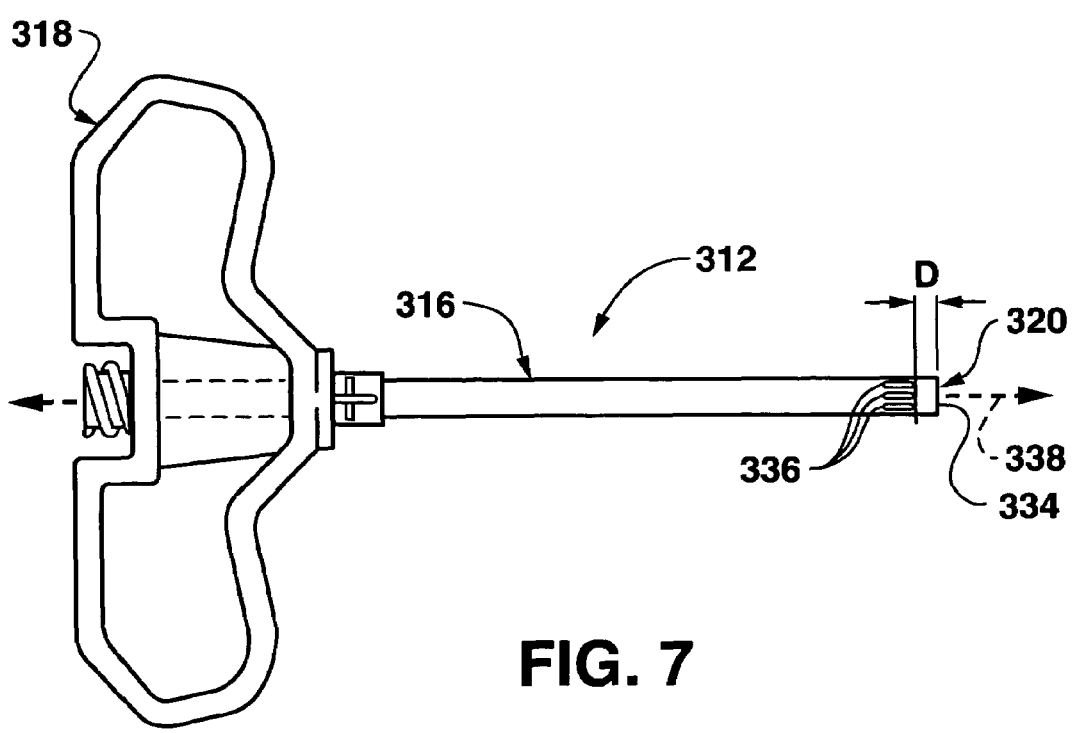
FIG. 7 is a side view of a further alternative bone graft needle according to the present invention.

The bone graft needle 312 illustrated in FIG. 7 is representative of a delivery member 316 having radial ports 336 that are not circular in perimetrical configuration. The radial ports 336 are formed as elongate slots in delivery member 316, and the slots begin a distance D proximally of the circumferential edge 334, which is disposed in a plane perpendicular to central longitudinal axis 338.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method of delivering bone graft paste material to a bone defect area in a patient's body through a minimally invasive portal, comprising:
   providing an instrument assembly for delivering the bone graft material to the bone defect area, said instrument assembly comprising:
      a bone graft needle for delivery of bone graft material to the bone defect area, said needle comprising an elongate tubular delivery member having a lumen between a proximal end and a distal end, said elongate tubular delivery member having a plurality of parts communicating with said lumen, said ports circumferentially positioned in a substantially circular band adjacent to said distal end, and
      an elongate penetrating member for receipt within said bone graft needle,
   inserting said elongate penetrating member into said lumen of said bone graft needle until a distal end of said elongate penetrating member extends from said distal end of said bone graft needle,
   inserting said instrument assembly through the minimally invasive portal until said open distal end of said bone graft needle operatively reaches the bone defect area, while maintaining said proximal end of said bone graft needle external of the patient's body,
   removing said elongate penetrating member from said bone graft needle while retaining said distal end of said bone graft needle at the bone defect area,
   forming a paste of bone graft material, said bone graft material comprising calcium sulfate, and
   using a syringe to inject said paste of bone graft material through said plurality of ports and said distal end of said bone graft needle to thereby deliver said bone graft material to the bone defect area.

2. A method of claim 1, wherein said bone graft material further comprises demineralized bone matrix.

3. The method of claim 1, wherein said bone graft needle has four ports.

4. The method of claim 1, wherein said ports are equally spaced about a longitudinal axis of said bone graft needle, to thereby provide an even and balanced distribution of bone graft material to the bone defect area.

5. The method of claim 1, wherein said ports are variably spaced about a longitudinal axis of said bone graft needle.

6. The method of claim 1, wherein each said port is circular.

7. The method of claim 1, wherein each said port is elongated in a direction substantially parallel to a longitudinal axis of said bone graft needle.

8. The method of claim 1, wherein a distal edge of each said port is positioned at a substantially equal distance from a proximal most edge of said distal end of said bone graft needle.

9. The method of claim 8, wherein said distance is between about 0.020 inch to about 0.275 inch.

10. The method of claim 9, wherein said distance is between about 0.082 inch to about 0.112 inch.

11. The method of claim 9, wherein each said port has a diameter of about 0.063 inch and said distance is between about 0.0505 inch to about 0.0805 inch.

12. The method of claim 1, wherein said bone graft needle has an external diameter of about 0.185 inch, said ports have a diameter of about 0.063 inch, said ports are equally spaced about a central longitudinal axis of said bone graft needle, and a center of each said port is located between about 0.082 inch and about 0.112 inch proximally of a proximal most edge of said distal end of said bone graft needle.

13. The method of claim 1, wherein said bone graft needle has an external diameter of about 0.115 inch, said ports have a diameter of about 0.047 inch, said ports are equally spaced about a central longitudinal axis of said bone graft needle, and a center of each said port is located between about 0.0882 inch and about 0.112 inch proximally of a proximal most edge of said distal end of said bone graft needle.

14. The method of claim 1, wherein said bone graft needle is made of a 304 series stainless steel, is about 4 inches in length, and has a J-type cannulated distal end.

15. The method of claim 1, wherein said needle is a 6 cm needle made of a 304 series stainless steel, is about 6 cm in length, and has a J-type cannulated distal end.

16. The method of claim 1, wherein said distal end of said bone graft needle is substantially blocked by abutment with bone or other anatomical tissue, yet plugging or clogging of the bone graft needle is avoided because said bone graft material discharges through said ports.

* * * * *